(12) United States Patent
Riedijk et al.

(10) Patent No.: US 11,935,319 B2
(45) Date of Patent: Mar. 19, 2024

(54) METHOD AND SYSTEM FOR FINGERPRINT SENSOR EVALUATION

(71) Applicant: FINGERPRINT CARDS ANACATUM IP AB, Gothenburg (SE)

(72) Inventors: Frank Riedijk, Delft (NL); Wouter Brevet, Delft (NL); Hans Thörnblom, Hålta (SE); Anton Landberg, Gothenburg (SE)

(73) Assignee: FINGERPRINT CARDS ANACATUM IP AB, Gothenburg (SE)

( * ) Notice: Subject to any disclaimer, the term of this patent is extended or adjusted under 35 U.S.C. 154(b) by 0 days.

(21) Appl. No.: 18/248,418

(22) PCT Filed: Nov. 2, 2021

(86) PCT No.: PCT/SE2021/051095
§ 371 (c)(1),
(2) Date: Apr. 10, 2023

(87) PCT Pub. No.: WO2022/098280
PCT Pub. Date: May 12, 2022

(65) Prior Publication Data
US 2023/0375612 A1    Nov. 23, 2023

(30) Foreign Application Priority Data
Nov. 5, 2020   (SE) .................................. 2051283-6

(51) Int. Cl.
*G06V 40/13* (2022.01)
*G01R 27/26* (2006.01)
(Continued)

(52) U.S. Cl.
CPC ..... *G06V 40/1306* (2022.01); *G01R 27/2605* (2013.01); *G01R 31/2829* (2013.01); *G06F 21/32* (2013.01)

(58) Field of Classification Search
CPC ............ G01R 31/2829; G01R 27/2605; G01R 27/26; G06F 21/32; G06V 40/1306;
(Continued)

(56) References Cited

U.S. PATENT DOCUMENTS 9,152,841 B1    10/2015  Riedijk
9,689,825 B1 *   6/2017  Lim ........................ G01N 27/24
(Continued)

FOREIGN PATENT DOCUMENTS

WO    2016163934 A1    10/2016

OTHER PUBLICATIONS

International Search Report and Written Opinion for International Application No. PCT/SE2021/051095, dated Jan. 20, 2022.
(Continued)

*Primary Examiner* — Premal R Patel
(74) *Attorney, Agent, or Firm* — Westman, Champlin & Koehler, P.A.

(57) ABSTRACT

A method of evaluating a dielectric structure, comprising the steps of a) changing a potential difference between each sensing structure in a first set of sensing structures and each sensing structure in a second set of sensing structures, and to providing, for each sensing structure in the first set of sensing structures, a sensing signal indicative of a strength of a capacitive coupling between each sensing structure in the second set of sensing structures and the sensing structure in the first set of sensing structures; b) assign other sensing structures to the first set of sensing structures and the second set of sensing structures; c) performing step a) and step b) until a respective sensing signal has been provided for each sensing structure in the plurality of sensing structures; and d) providing an evaluation result based on the respective sensing signals.

15 Claims, 6 Drawing Sheets

(51) Int. Cl.
*G01R 31/28* (2006.01)
*G06F 21/32* (2013.01)

(58) Field of Classification Search
CPC .......... G06V 10/98; G06V 40/12–1394; A61B 2562/02; A61B 5/1172
See application file for complete search history.

(56) References Cited

U.S. PATENT DOCUMENTS

| | | |
|---|---|---|
| 9,779,278 B2 | 10/2017 | Nilsson |
| 9,971,930 B2 | 5/2018 | Östlund |
| 2003/0042911 A1 | 3/2003 | Lane et al. |
| 2008/0208495 A1 | 8/2008 | Xu |
| 2014/0218056 A1 | 8/2014 | Alatas et al. |
| 2016/0300095 A1 | 10/2016 | Nilsson |
| 2017/0330013 A1 | 11/2017 | Ramberg et al. |
| 2018/0012053 A1 | 1/2018 | Larsson et al. |
| 2018/0136271 A1* | 5/2018 | Philipson ............. H03K 17/962 |
| 2018/0137324 A1* | 5/2018 | Riedijk ............. G06V 40/1306 |

OTHER PUBLICATIONS

Extended European Search Report dated Dec. 6, 2022, for corresponding European Application No. 2 21889713.0, 7 pages.

\* cited by examiner

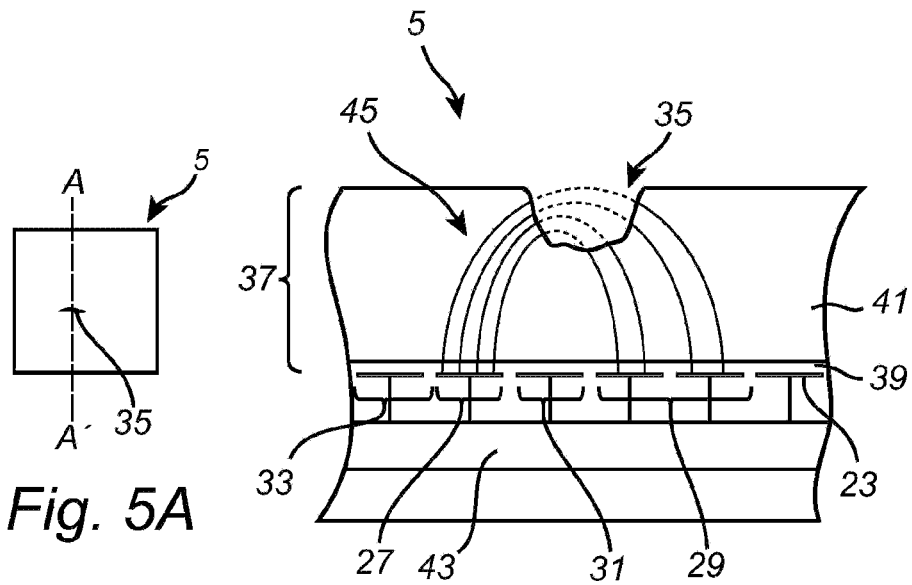
Fig. 5A
Fig. 5B
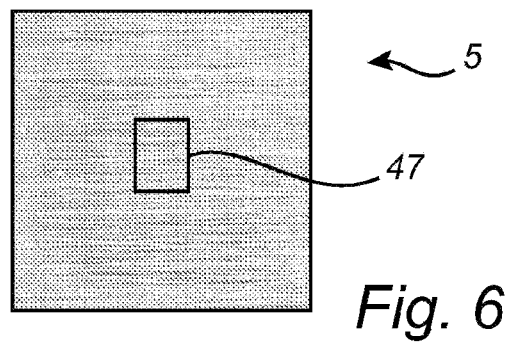
Fig. 6
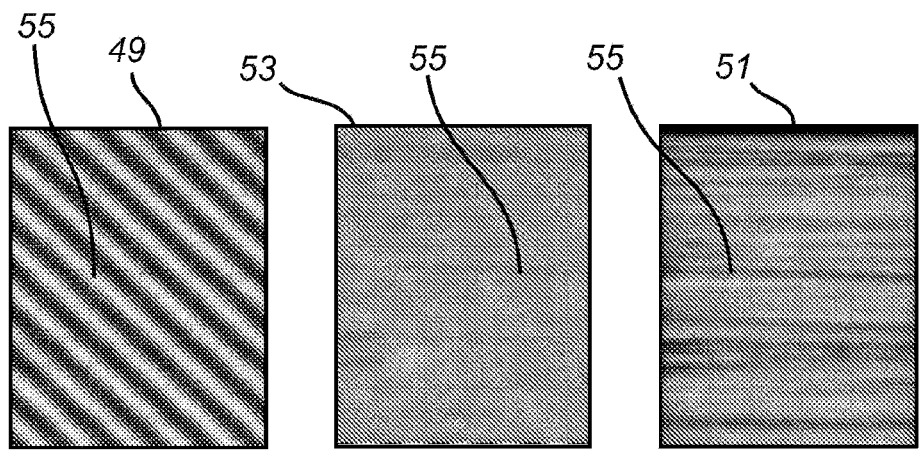
Fig. 7A   Fig. 7B   Fig. 7C

METHOD AND SYSTEM FOR FINGERPRINT SENSOR EVALUATION

CROSS-REFERENCE TO RELATED APPLICATION

This Application is a Section 371 National Stage Application of International Application No. PCT/SE2021/051095, filed Nov. 2, 2021, which claims priority to Swedish Patent Application No. 2051283-6 filed on Nov. 5, 2020, and published as WO 2022/098280 A1 on May 12, 2022, in English, the entire contents of which are hereby incorporated by reference in their entireties.

FIELD OF THE INVENTION

The present invention relates to a method of evaluating a dielectric structure covering a plurality of sensing structures comprised in a fingerprint sensor and defining a finger receiving surface of the fingerprint sensor, and to a fingerprint sensor evaluation system.

BACKGROUND OF THE INVENTION

Various types of biometric systems are used more and more in order to provide for increased security and/or enhanced user convenience.

In particular, fingerprint sensing systems have been adopted in, for example, consumer electronic devices, thanks to their small form factor, high performance and user acceptance.

Among the various available fingerprint sensing principles (such as capacitive, optical, acoustic, thermal etc), capacitive sensing is most commonly used, in particular in applications where size and power consumption are important issues.

Capacitive fingerprint sensors generally provide a measure indicative of the capacitance between each of several sensing structures and a finger placed on or moved across the surface of the fingerprint sensor.

A consequence of this is that whatever is present between the sensing structures and the finger will strongly influence the ability of the capacitive fingerprint sensor to provide a true and useful representation of the fingerprint of the finger placed on the structure on top of the sensing structures. Anomalies, such as a material thickness that is outside of specifications, various defects such as scratches or bubbles, and dielectric or conductive structures that may have been arranged on top of the sensor coating, may degrade the performance of the authentication system including the sensor, negatively affecting the user experience.

As a part of the process of fingerprint sensor packaging, a test procedure is typically carried out, involving touching the fingerprint sensor surface with a soft stamp and making a regular fingerprint sensor reading, like when acquiring a fingerprint representation from the fingerprint sensor. Hereby, various anomalies, such as the above-mentioned coating defects or thickness variations, can be detected, and defective fingerprint sensors can be rejected or reworked. Such a test procedure is described in U.S. Pat. No. 9,971,930.

It would be desirable to provide a fingerprint sensor evaluation method that can provide an evaluation result for the dielectric structure covering the sensing structures without the need for touching each sensor with a stamp as described above.

Further, it would be desirable to provide for evaluation of the dielectric structure covering the sensing structures after the fingerprint sensor has been integrated in a product and delivered to a customer.

SUMMARY

In view of the above-mentioned and other drawbacks of the prior art, it is an object of the present invention to provide for improved evaluation of the dielectric structure covering the sensing structures in a capacitive fingerprint sensor.

According to a first aspect of the present invention, it is therefore provided a method of evaluating a dielectric structure covering a plurality of sensing structures comprised in a fingerprint sensor and defining a finger receiving surface of the fingerprint sensor, the method comprising the steps of:

a) controlling the fingerprint sensor to change a potential difference between each sensing structure in a first set of sensing structures and each sensing structure in a second set of sensing structures, and to provide, for each sensing structure in the first set of sensing structures, a sensing signal indicative of a strength of a capacitive coupling between each sensing structure in the second set of sensing structures and the sensing structure in the first set of sensing structures;

b) controlling the fingerprint sensor to assign other sensing structures to the first set of sensing structures and the second set of sensing structures;

c) performing step a) and step b) until a respective sensing signal has been provided for each sensing structure in the plurality of sensing structures; and d) providing an evaluation result for the dielectric structure covering the plurality of sensing structures based on the respective sensing signals provided for each sensing structure in the plurality of sensing structures.

The present invention is based on the realization that the capacitive coupling between different sensing structures in the fingerprint sensor is representative of the electrical properties of the material between the sensing structures, and that the dielectric structure covering the plurality of sensing structures can be evaluated by sensing such capacitive couplings across the sensor surface without placing anything on the finger receiving surface of the fingerprint sensor. In particular, there is no need for any physical object touching the finger receiving surface of the fingerprint sensor.

Hereby, production test of packaged fingerprint sensors can be made faster and more accurate, resulting in a more cost-efficient production of packaged fingerprint sensors and/or electronic systems, such as smart cards etc, including fingerprint sensors.

Furthermore, since there is no need to touch the finger receiving surface with a stamp or probe having well-defined and know properties when evaluating the fingerprint sensor, embodiments of the present invention enable evaluation of the dielectric structure covering the sensing structures even after delivery of the product including the fingerprint sensor to the end user. This may be useful for diagnostics, as well as for adaptive fingerprint image processing that may reduce the effects of anomalies in the material stack-up covering the sensing structures of the fingerprint sensor. For example, defects that have occurred when the product including the fingerprint sensor has been in use may be compensated for, and attacks on the fingerprint authentication by attaching conductive structures to the fingerprint sensor can be detected and defeated.

It should be noted that the above-mentioned "plurality" of sensing structures comprised in the fingerprint sensor need not necessarily be "all" of the sensing structures comprised in the fingerprint sensor. In some cases it may be sufficient or beneficial to evaluate the dielectric structure based on sensing signals from a sub-set of "all" of the sensing structures. For instance, it may sometimes be sufficient to use for example one half, or one third, or a smaller fraction of the sensing structures substantially evenly distributed across a sensing area of the fingerprint sensor. In other situations, it may be beneficial to use a sub-set of sensing structures occupying a contiguous sub-area of the sensing area. This may, for example, be the case if it is known where in the sensing area there is an anomaly in the dielectric structure. Such knowledge may, for example, be obtained through an initial or preliminary evaluation using a sub-set of substantially evenly distributed sensing structures.

According to various embodiments, step d) may further comprise forming a representation of the dielectric structure based on the respective sensing signals provided for each sensing structure in the plurality of sensing structures; and the evaluation result may be provided based on the representation of the dielectric structure. This representation may advantageously by an image, such as a gray scale image.

According to embodiments, furthermore, steps a) to c) may be performed for at least two different configurations of at least one of the first set of sensing structures and the second set of sensing structures; and the evaluation result provided in step d) may be based on the respective sensing signals provided for each sensing structure in the plurality of sensing structures for each of the at least two different configurations.

In these embodiments, steps a)-c) may first be performed for a first configuration, and then for a second configuration. Alternatively, step a) may first be performed for each configuration, before proceeding to step b).

The different configurations may contain different numbers of sensing structures and/or different layouts of sensing structures and/or different spatial relationships between the sensing structures in the first set and the sensing structures in the second set. In a simple example, two different configurations may differ only in a distance between the first set and the second set. The different configurations can be selected to result in different electrostatic fields between the sensing structure(s) in the first set and the sensing structure(s) in the second set. Different electrostatic fields may be utilized for evaluating anomalies in the dielectric structure at different depths and/or with different electrical properties.

In various embodiments, each sensing structure in the first set of sensing structures may be separated from each sensing structure in the second set of sensing structures by at least one intermediate sensing structure.

By controlling a potential of the at least one intermediate sensing structure in relation to the potential of each sensing structure in the first set of sensing structures and the potential of each sensing structure in the second set of sensing structures, the electric field line configuration can be controlled. Hereby, it can be controlled which part of the dielectric structure (along a normal to the sensing surface where the sensing structures are arranged) that is evaluated.

According to a second aspect of the present invention, there is provided a fingerprint sensor evaluation system for evaluating a dielectric structure covering a plurality of sensing structures comprised in a fingerprint sensor and defining a finger receiving surface of the fingerprint sensor, the fingerprint sensor evaluation system comprising: a fingerprint sensor interface for communication with the fingerprint sensor; and processing circuitry coupled to the fingerprint sensor interface, wherein the processing circuitry is configured to: acquire an image from the fingerprint sensor while the finger receiving surface of the fingerprint sensor remains untouched by a physical object; evaluate the dielectric structure covering the plurality of sensing structures in the fingerprint sensor based on the acquired image; and provide a result of the evaluation.

The fingerprint evaluation system may be included in a fingerprint sensing system for determining a fingerprint representation of a finger, the fingerprint sensing system further comprising a fingerprint sensor comprising a plurality of sensing structures covered by a dielectric structure, the fingerprint sensor being controllable between: an evaluation mode in which an image provided by the fingerprint sensor indicates, for each sensing structure in the plurality of sensing structures, a capacitive coupling between the sensing structure and at least one other sensing structure in the plurality of sensing structures; and a fingerprint sensing mode in which an image provided by the fingerprint sensor indicates, for each sensing structure in the plurality of sensing structures, a capacitive coupling between the sensing structure and the finger. In the fingerprint sensing system, the fingerprint evaluation system is connected to the fingerprint sensor and configured to: control the fingerprint sensor to the evaluation mode and acquire a first image; control the fingerprint sensor to the fingerprint sensing mode and acquire a second image; modify the second image based on the first image to form a modified second image; and determine the fingerprint representation based on the modified second image.

The finger sensing system may, moreover, advantageously be included in an electronic device further comprising processing circuitry configured to: acquire a fingerprint representation from the fingerprint sensing system; authenticate a user based on the fingerprint representation; and perform at least one user-requested process only if the user is authenticated based on the representation. The electronic device may, for example, be a handheld communication device, such as a mobile phone or a tablet, a computer, or an electronic wearable item such as a watch or similar, or a smart card.

In summary, the present invention relates to a method of evaluating a dielectric structure, comprising the steps of a) changing a potential difference between each sensing structure in a first set of sensing structures and each sensing structure in a second set of sensing structures, and to providing, for each sensing structure in the first set of sensing structures, a sensing signal indicative of a strength of a capacitive coupling between each sensing structure in the second set of sensing structures and the sensing structure in the first set of sensing structures; b) assign other sensing structures to the first set of sensing structures and the second set of sensing structures; c) performing step a) and step b) until a respective sensing signal has been provided for each sensing structure in the plurality of sensing structures; and d) providing an evaluation result based on the respective sensing signals.

BRIEF DESCRIPTION OF THE DRAWINGS

These and other aspects of the present invention will now be described in more detail, with reference to the appended drawings showing an example embodiment of the invention, wherein:

FIG. 5A illustrates a fingerprint sensor with a coating anomaly, here in the form of a scratch;

FIG. 5B is a schematic enlarged cross-section view of a portion of the fingerprint sensor in FIG. 5A;

FIG. 6 is an illustration of a scratched fingerprint sensor used in a benchmarking test of the evaluation method according to an embodiment of the present invention;

FIGS. 7A-C are illustrations of images obtained from the sensor in FIG. 6 using conventional methods (FIGS. 7A-B) and the method according to an embodiment of the present invention (FIG. 7C)

DETAILED DESCRIPTION OF EXAMPLE EMBODIMENTS

Figure 1A:
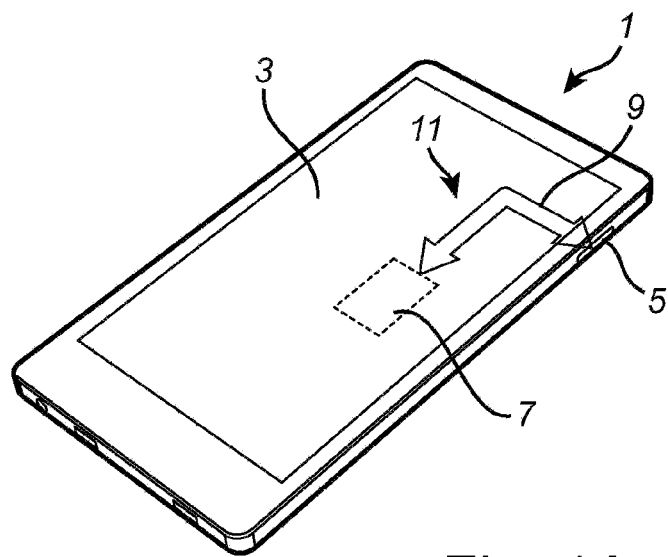
FIGS. 1A-C illustrate exemplary devices including fingerprint sensor evaluation systems according to various embodiments of the present invention.
Figure 1B:
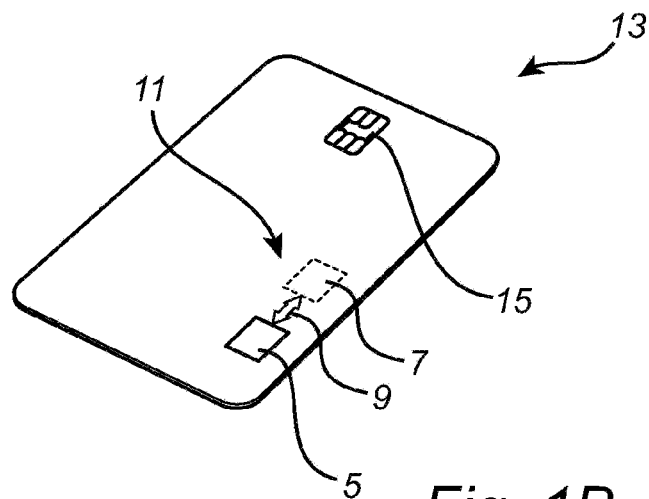
Figure 1C:
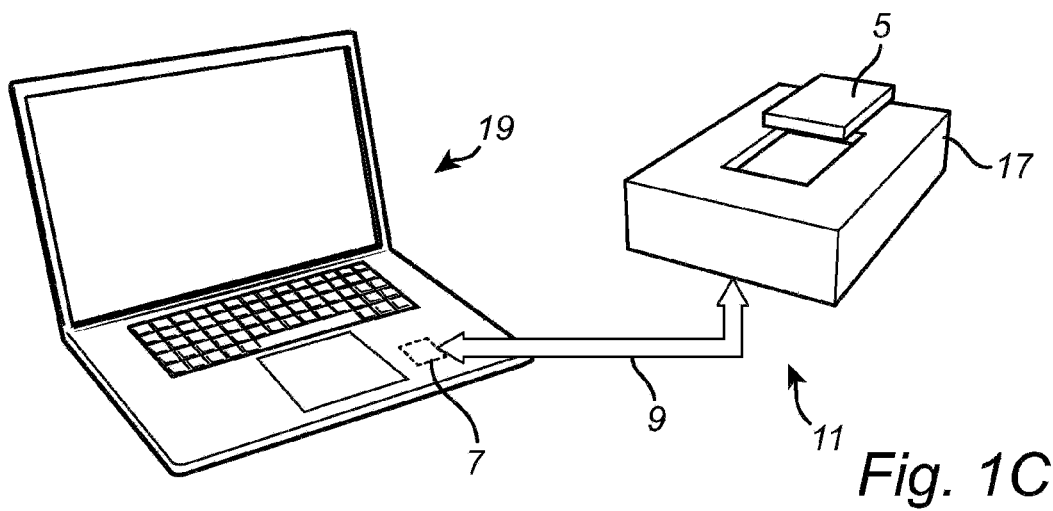

FIGS. 1A-C illustrate exemplary devices including fingerprint sensor evaluation systems according to various embodiments of the present invention.

FIG. 1A shows a mobile phone 1 including a touch screen 3, a fingerprint sensor 5, processing circuitry 7 schematically indicated as a dashed-line box, and a fingerprint sensor interface 9 schematically indicated as a double arrow for allowing the processing circuitry 7 to communicate with the fingerprint sensor 5. An example embodiment of the fingerprint sensor evaluation system 11 according to the present invention may include the fingerprint sensor interface 9 and the processing circuitry 7.

FIG. 1B shows a smart card 13 here illustrated as including a contact area 15, a fingerprint sensor 5, processing circuitry 7, and fingerprint sensor interface 9. It should be noted that the smart card 13 may additionally or alternatively be configured for contactless operation in accordance with applicable standards. An example embodiment of the fingerprint sensor evaluation system 11 according to the present invention may include the fingerprint sensor interface 9 and the processing circuitry 7.

FIG. 1C shows a fingerprint sensor evaluation system 11 in the form of a production test arrangement for production testing of packaged fingerprint sensors. The fingerprint sensor evaluation system 11 in FIG. 1C includes a test fixture 17 for receiving a packaged fingerprint sensor 5, a computer 19 including processing circuitry 7 connectable to the packaged fingerprint sensor 5 via a fingerprint sensor interface 9.

Figure 2:
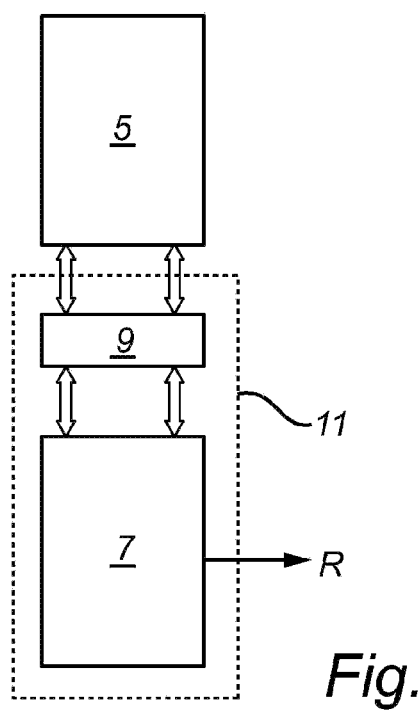
FIG. 2 is a schematic functional block diagram of a fingerprint sensor evaluation system according to embodiments of the present invention.

FIG. 2 is a schematic functional block diagram of a fingerprint sensor evaluation system 11 according to embodiments of the present invention, for evaluating a dielectric structure covering a plurality of sensing structures comprised in a fingerprint sensor 5 and defining a finger receiving surface of the fingerprint sensor 5.

The fingerprint sensor evaluation system 11 comprises a fingerprint sensor interface 9 for communication with the fingerprint sensor 5, and processing circuitry 7 coupled to the fingerprint sensor interface 9. As will be described in greater detail further below, the processing circuitry 7 is configured to acquire an image from the fingerprint sensor 5 while the finger receiving surface of the fingerprint sensor 5 remains untouched by a physical object, evaluate the dielectric structure covering the plurality of sensing structures in the fingerprint sensor 5 based on the acquired image; and provide a result R of the evaluation.

In some embodiments of the present invention, the above-described fingerprint sensor evaluation system 11 may be comprised in a fingerprint sensing system for determining a fingerprint representation of a finger. Such a fingerprint sensing system may comprise a fingerprint sensor 5, and may suitably be included in an electronic device, such as the above-described mobile phone 1 or smart card 13. The electronic device (such as the mobile phone 1 or smart card 13) may comprise processing circuitry 7 configured to acquire a fingerprint representation from the fingerprint sensing system, authenticate a user based on the fingerprint representation; and perform at least one user-requested process only if the user is authenticated based on the representation.

To that end, the fingerprint sensor 5 may advantageously be controllable between an evaluation mode in which an image provided by the fingerprint sensor 5 indicates, for each sensing structure in the plurality of sensing structures, a capacitive coupling between the sensing structure and at least one other sensing structure in the plurality of sensing structures, and a fingerprint sensing mode in which an image provided by the fingerprint sensor 5 indicates, for each sensing structure in the plurality of sensing structures, a capacitive coupling between the sensing structure and the finger. Fingerprint sensors 5, which are controllable to selectively apply one of several different potentials to each sensing structure are, per se, well known to those of ordinary skill in the art. One example of such fingerprint sensors 5 is described in U.S. Pat. No. 9,152,841, which is hereby incorporated by reference in its entirety.

Illustrative examples of a fingerprint sensor 5 operating in the fingerprint sensing mode and the evaluation mode will now be described with reference to FIGS. 3A-B, respectively.

Figure 3:
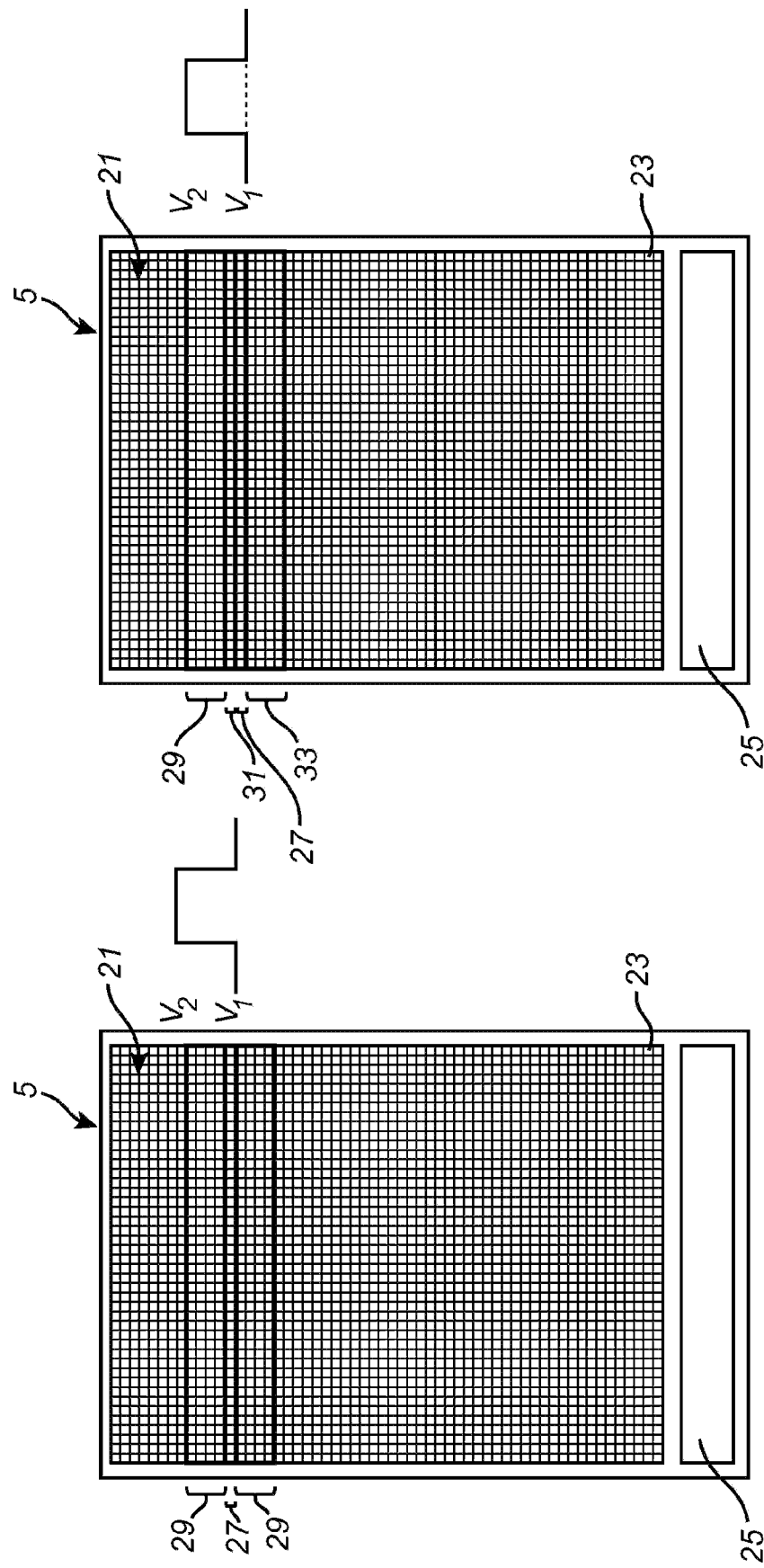
FIG. 3A is a schematic illustration of a fingerprint sensor operating in a fingerprint sensing mode.
FIG. 3B is a schematic illustration of a fingerprint sensor operating in an evaluation mode.

Turning first to FIG. 3A, schematically illustrating a capacitive fingerprint sensor 5 operating in the fingerprint sensing mode, the fingerprint sensor 5 comprises a sensor array 21 with a plurality of sensing structures 23 (only one of the sensing structures 23 is indicated by a reference numeral to avoid cluttering the drawings), and readout circuitry 25 coupled to the sensor array 21 for acquiring sensing signals from the sensor array 21. Each of the sensing structures 23 is controllable to exhibit at least a first potential V1 and a second potential V2, in relation to a reference potential of the fingerprint sensor 5.

Furthermore, each of the sensing structures 23 is controllable to provide a sensing signal to the readout circuitry 25. Depending on the operational mode and circumstances (such as whether or not a finger is arranged on the sensor array 21), the sensing signal will carry different information about the surroundings of the sensing structure 23 providing the sensing signal.

Referring to the example configuration of the fingerprint sensing mode in FIG. 3A, the fingerprint sensor 5 is illustrated in a state where it is presently controlled to change a potential of each sensing structure in a first set 27 of sensing structures (here a row of sensing structures) and each sensing structure in a second set 29 of sensing structures (here several rows on each side of the first set 27 of sensing structures) from the first potential V1 to the second potential V2, and then back from the second potential V2 to the first potential V1. This is schematically illustrated in the curve form diagram to the right in FIG. 3A. In connection with this change in potential (either from the first potential V1 to the second potential V2 or from the second potential V2 to the first potential V1), sensing signals for each sensing structure in a first set 27 of sensing structures are acquired by the readout circuitry 25. When a finger is placed on the fingerprint sensor 5, the sensing signals for the different sensing structures in the first set 27 of sensing structures indicate the strength of the capacitive coupling between the finger and the different sensing structures, from which a representation (such as an image) of the partial fingerprint facing the portion of the sensor surface currently occupied by the first set 27 of sensing structures can be determined. By controlling the fingerprint sensor 5 so that the first 27 and second 29 sets of sensing structures scan the sensor array 21 (from top to bottom, or bottom to top, or any other sequence), a fingerprint representation, such as a fingerprint image, from the full sensor array 21 can be acquired. A reason for controlling the fingerprint sensor 5 as described above is to prevent or at least substantially reduce the effect on the sensing signals from any capacitive coupling between different sensing structures 23 in the sensor array 21. This improves the fingerprint image acquisition.

FIG. 3B schematically illustrates the capacitive fingerprint sensor 5 operating in the evaluation mode, and is illustrated in a state where it is presently controlled to change a potential of each sensing structure in a first set 27 of sensing structures (here a row of sensing structures) from a first potential V1 to a second potential V2 and then back from the second potential V2 to the first potential V1, and to keep a potential of each sensing structure in a second set 29 of sensing structures (here several rows on one side of the first set 27 of sensing structures) at the first potential V1. This is schematically illustrated in the curve form diagram to the right in FIG. 3B. As is indicated in FIG. 3B, there is an intermediate third set 31 of sensing structures arranged between the first set 27 of sensing structures and the second set 29 of sensing structures. There is also a fourth set 33 of sensing structures on the other side of the first set 27 of sensing structures, in relation to the second set 29 of sensing structures. In the example configuration of FIG. 3B, the fingerprint sensor 5 is controlled to change a potential of each sensing structure in the third set 31, and the fourth set 33 of sensing structures from the first potential V1 to the second potential V2, in synchronization with the control of the sensing structures in the first set 27 of sensing structures.

In connection with this change in potential (either from the first potential V1 to the second potential V2 or from the second potential V2 to the first potential V1), sensing signals for each sensing structure in a first set 27 of sensing structures are acquired by the readout circuitry 25. When the fingerprint sensor 5 is not touched by a finger or other object, the sensing signals for the different sensing structures in the first set 27 of sensing structures indicate the strength of the capacitive coupling between the sensing structures in the first set 27 and the sensing structures in the second set 29, from which a representation (such as an image) can be determined of a portion of a dielectric structure covering a the sensing structures and being arranged between the sensing structures in the first set 27 and the sensing structures in the second set 29.

By controlling the fingerprint sensor 5 so that the first 27, second 29, third 31, and fourth 33 sets of sensing structures scan the sensor array 21 (from top to bottom, or bottom to top, or any other sequence), a representation, such as an image of the dielectric structure covering substantially the whole sensor array 21 can be acquired.

In connection with FIG. 3B, it has been described that fingerprint sensor 5 is controlled in such a way that the potential of each sensing structure in the first set 27 of sensing structures is changed between the first potential V1 and the second potential V2, and the potential of each sensing structure in the second set 29 of sensing structures remains at the first potential V1. It should be noted that this is only one possible configuration, and that, for example, the fingerprint sensor 5 may equally well be controlled in such a way that the potential of each sensing structure in the second set 29 of sensing structures is changed between the first potential V1 and the second potential V2, and the potential of each sensing structure in the first set 27 of sensing structures remains at the first potential V1. This alternative driving scheme may be preferable, since the fingerprint sensor 5 may be less complicated to control to achieve this driving pattern.

Although the different sets of sensing structures have been exemplified as rows above, it should be noted that the different sets may alternatively have other configurations, such as parts of rows, columns or parts of columns, or any other configuration deemed to be useful based on circuit simulation and or tests.

Figure 4:
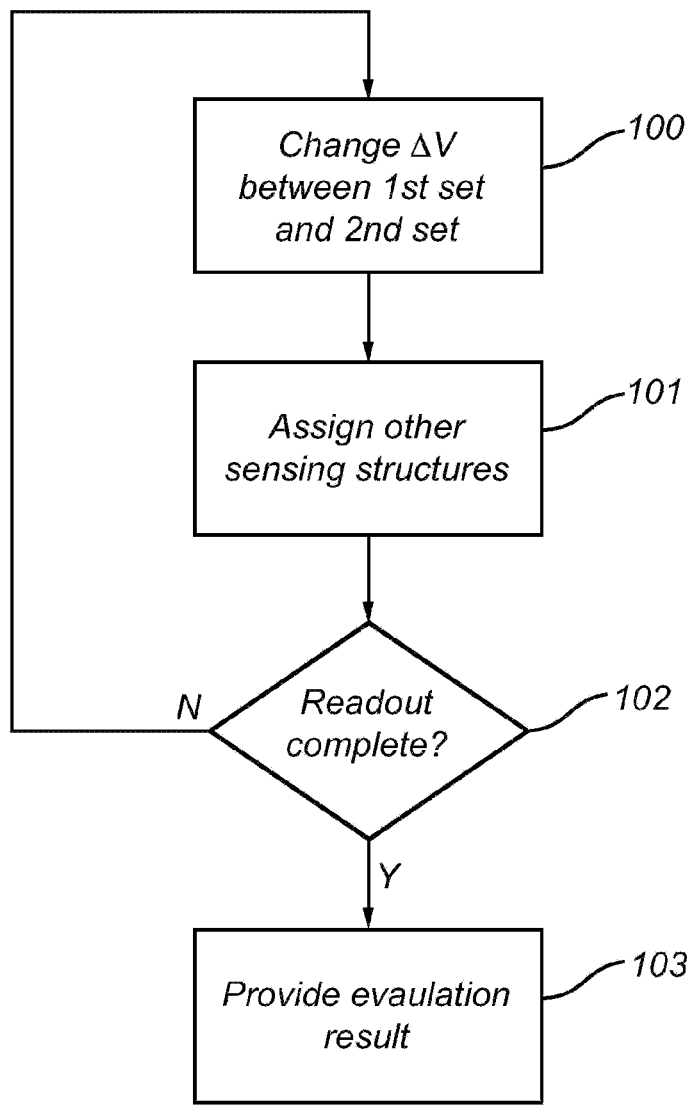
FIG. 4 is a flow-chart illustrating a method according to an example embodiment of the present invention.

An example embodiment of the method according to the present invention will be described below with reference to the flow-chart in FIG. 4, and additional illustrations where indicated.

In a first step 100, initially additionally referring to FIG. 3B, the fingerprint sensor 5 is controlled to change a potential difference between each sensing structure in a first set 27 of sensing structures and each sensing structure in a second set 29 of sensing structures, and to provide, for each sensing structure in the first set 27 of sensing structures, a sensing signal indicative of a strength of a capacitive coupling between each sensing structure in the second set 29 of sensing structures and the sensing structure in the first set 27 of sensing structures. In the exemplary configuration described above with reference to FIG. 3B, the change in potential difference is from 0V (when the sensing elements in the first set 27 and the sensing elements in the second set 29 are controlled to the first potential V1) to V2-V1 (when the sensing elements in the first set 27 have been controlled from the first potential V1 to the second potential V2, and the sensing elements in the second set 29 remain at the first potential V1).

In the subsequent step 101, the fingerprint sensor 5 is controlled to assign other sensing structures to the first set 27 of sensing structures and the second set 29 of sensing structures.

In step 102, it is determined if the readout from the fingerprint sensor 5 is complete, that is, if a respective sensing signal has been provided for each sensing structure 23 in the plurality of sensing structures.

If this is not the case, the method returns to step 101. If the readout is complete, the method instead proceeds to step 103, where an evaluation result is provided for the dielectric structure covering the plurality of sensing structures 23 based on the respective sensing signals provided for each sensing structure in the plurality of sensing structures.

Through the method according to embodiments of the present invention, properties of the dielectric structure covering the sensing structures 23 of the fingerprint sensor 5 can be evaluated without the need for arranging a conductive member with known properties on top of the dielectric structure.

FIG. 5A illustrates a fingerprint sensor 5 with a coating anomaly, here in the form of a scratch 35, and FIG. 5B is a schematic enlarged cross-section view of a portion of the fingerprint sensor in FIG. 5A, where the cross-section is taken along the line A-A' in FIG. 5A.

Referring to FIG. 5B, the fingerprint sensor 5 is schematically shown to comprise a dielectric structure 37 covering the sensing structures 23. As is indicated in FIG. 5B, the dielectric structure 37 comprises a passivation layer 39 and a protective coating 41 applied in the process of packaging the fingerprint sensor 5. It should be noted that this is merely a schematic illustration of an example configuration, or stack-up, of the dielectric structure 37, and that the dielectric structure 37 may comprise additional whole or partial layers that may have been added during production of the fingerprint sensor 5 or after integration of the fingerprint sensor 5 in an electronic device, such as the mobile phone 1 in FIG. 1A or the smart card 13 in FIG. 1B.

In addition, the fingerprint sensor 5 comprises measurement circuitry 43 connected to each sensing structure 23 for providing selected potentials (such as the above-mentioned first V1 and second V2 potentials) to the sensing structures 23 and providing sensing signals for the sensing structures in the first set 27 to the readout circuitry 25. The measurement circuitry 43 is not described in detail herein, because it is well known in the art how potentials can be applied to selected sensing structures 23, and sensing signals can be read out in a capacitive fingerprint sensor 5.

In this context, it should be noted that the fingerprint sensor 5 may be controlled by the fingerprint sensor evaluation system 11 in different ways. According to one example, the readout circuitry 25 and the measurement circuitry 43 of the fingerprint sensor 5 may be directly controlled by the fingerprint evaluation system 11. According to another example, the readout circuitry 25 and the measurement circuitry 43 may be indirectly controlled by the fingerprint evaluation system 11. For instance, the fingerprint evaluation system 11 may provide a mode signal to set the fingerprint sensor in the above-mentioned evaluation mode, and then provide a readout command to the fingerprint sensor 5. In response, the fingerprint sensor 5 may independently scan through the sensing structures 23 in the sensor array 21 as described above and provide an evaluation result, for example in the form of a gray scale image, to the fingerprint evaluation system 11.

Since the cross-section A-A' runs through the rows of the fingerprint sensor 5, each row of sensing structures 23 in the fingerprint sensor 5 is represented by a single sensing structure 23 in FIG. 5B. The above-mentioned first 27, second 29, third 31, and fourth 33 sets of sensing structures are indicated in FIG. 5B for an example configuration, together with exemplary field lines 45 of the electrostatic field resulting from the above-mentioned change in potential difference between the sensing structures in the first set 27 of sensing structures and the sensing structures in the second set 29 of sensing structures.

For the kind of coating anomaly, in the form of scratch 35, in FIGS. 5A-B, the dielectric constant "inside" the scratch 35 is considerably lower than the dielectric constant of the protective coating 41 surrounding the scratch 35. Therefore the strength of the capacitive coupling (indicated by the field lines 45) between the sensing structures in the first set 27 of sensing structures and the sensing structures in the second set 29 of sensing structures at the scratch 35 will be considerably lower than the strength of the capacitive coupling where there is no scratch.

Experiments reveal that this difference in strength of capacitive coupling is clearly visible, and can be used to evaluate the dielectric structure 37 and/or compensate for defects in the dielectric structure 37.

FIG. 6 is an illustration of a scratched fingerprint sensor 5 used in a benchmarking test of the evaluation method according to an embodiment of the present invention, and FIGS. 7A-C are illustrations of partial images of the central portion 47 obtained from the sensor 5 in FIG. 6 using conventional methods (FIGS. 7A-B) and the method according to an embodiment of the present invention (FIG. 7C).

In particular, the image 49 in FIG. 7A was taken using the fingerprint sensor 5 in FIG. 6 operating in the fingerprint sensing mode while being contacted with a conductive stamp with a striped pattern, and the image 51 in FIG. 7B was taken using the fingerprint sensor 5 in FIG. 6 operating in the fingerprint sensing mode while being contacted with a conductive stamp with a uniform pattern (a flat stamp). The image 53 in FIG. 7C was taken using the fingerprint sensor 5 in FIG. 6 operating in the evaluation mode described above, while not being covered. Studying the different images 49, 51, 53, the scratches 55 are discernible in all of them, but most clearly in the image 53 taken using the method according to an example embodiment of the present invention.

In the particular example in FIG. 7C, the first set 27 of sensing structures was a single row (at a time), the second set 29 of sensing structures comprised seven rows, the third set 31 of sensing structures comprised one row, and the fourth set 33 of sensing structures comprised eight rows. It should be noted, however, that this is only an example of sensing structure voltage/potential configuration and that other configurations may work equally well, or better depending on, for example, the properties of the dielectric structure 37 and/or the kind and location of the coating anomaly or anomalies.

Figure 8A:
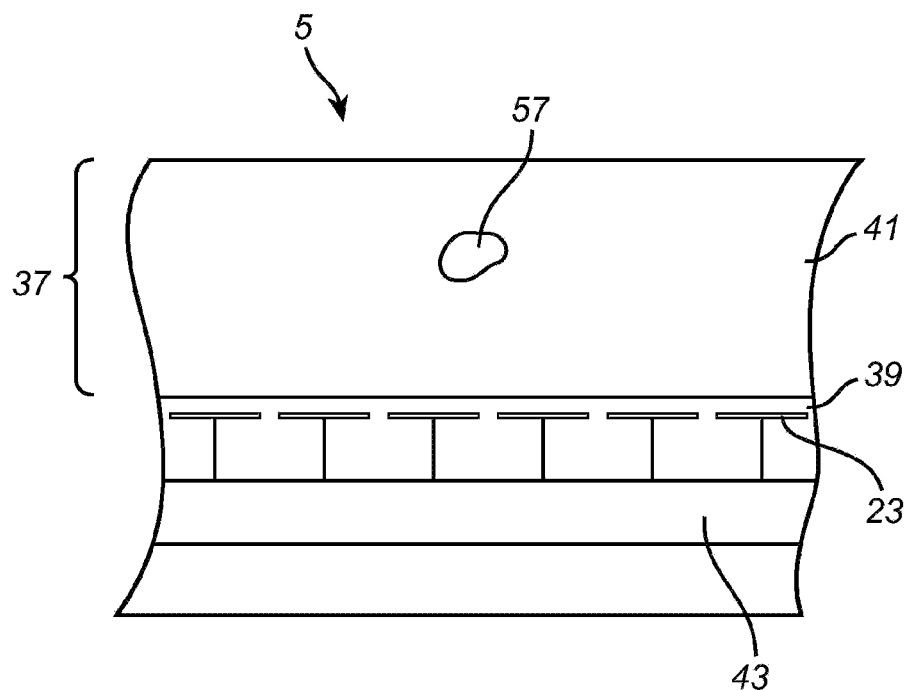
FIGS. 8A-B illustrate other possible anomalies that may detected using the method according to embodiments of the present invention.
Figure 8B:
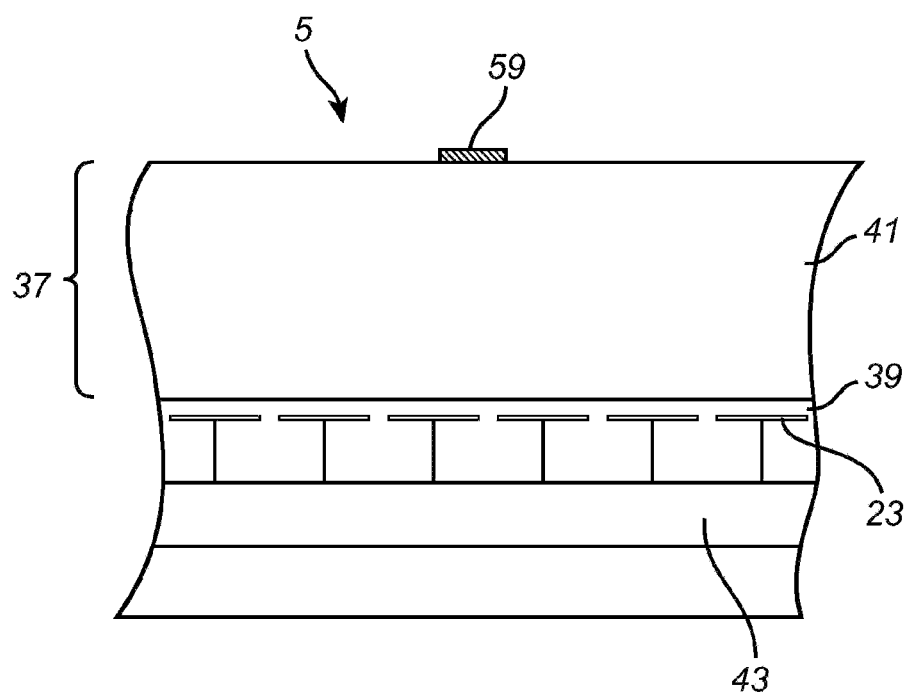

FIGS. 8A-B illustrate other possible anomalies that may be detected using the method according to embodiments of the present invention. In FIG. 8A, the protective coating 41 of the fingerprint sensor 5 has a bubble 57 that may be better imaged using a sensing structure voltage/potential configuration resulting in field lines localized closer to the sensing structures 23. This may, for example, be achieved by dispensing with the third set 31 of sensing structures. In FIG. 8B, a conductive structure 59 may have been provided on the dielectric structure 37, as part of a so-called attack pattern, after integration of the fingerprint sensor 5 in an electronic device, such as the mobile phone 1 in FIG. 1A or the smart card 13 in FIG. 1B. Such a conductive structure 59 will affect the field lines between the sensing structures in the first set 27 and the sensing structures in the second set 29, and can thus be detected using the method according to embodiments of the present invention.

In various cases, such as when evaluating a fingerprint sensor in which different kinds of anomalies may be present (such as the example anomalies indicated in FIGS. 5A-B and FIGS. 8A-B), it may be beneficial to perform the evaluation with different configurations of the first and/or second sets of sensing structures. As will apparent to one of ordinary skill in the art, it will be straight-forward to define configurations that will provide different amounts of spatial averaging or electrostatic field lines that are mainly located at different depths of the dielectric structure, etc.

After the fingerprint sensor 5 has been integrated in an electronic device, the above-described evaluation of the dielectric structure 37 may advantageously be used for improving the fingerprint representation acquired using the fingerprint sensor 5 in the fingerprint sensing mode. Accordingly, the fingerprint evaluation system 11 may be configured to control the fingerprint sensor 5 to the evaluation mode and acquire a first image, control the fingerprint sensor 5 to the fingerprint sensing mode and acquire a second image, modify the second image based on the first image to form a modified second image; and determine the fingerprint representation based on the modified second image. The first image should be acquired without a finger on the fingerprint sensor 5. Of course, the order of the image acquisitions may be reversed.

The person skilled in the art realizes that the present invention by no means is limited to the preferred embodiments described above. On the contrary, many modifications and variations are possible within the scope of the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of evaluating a dielectric structure covering a plurality of sensing structures comprised in a fingerprint sensor and defining a finger receiving surface of the fingerprint sensor, the method comprising the steps of:
   a) controlling the fingerprint sensor to change a potential difference between each sensing structure in a first set of sensing structures and each sensing structure in a second set of sensing structures, and to provide, for each sensing structure in the first set of sensing structures, a sensing signal indicative of a strength of a capacitive coupling between each sensing structure in the second set of sensing structures and the sensing structure in the first set of sensing structures;
   b) controlling the fingerprint sensor to assign other sensing structures to the first set of sensing structures and the second set of sensing structures;
   c) performing step a) and step b) until a respective sensing signal has been provided for each sensing structure in the plurality of sensing structures; and
   d) providing an evaluation result for the dielectric structure covering the plurality of sensing structures based on the respective sensing signals provided for each sensing structure in the plurality of sensing structures.

2. The method according to claim 1, wherein:
   step d) further comprises forming a representation of the dielectric structure based on the respective sensing signals provided for each sensing structure in the plurality of sensing structures; and
   the evaluation result is provided based on the representation of the dielectric structure.

3. The method according to claim 2, wherein the representation is a gray scale image.

4. The method according to claim 1, wherein:
   steps a) to c) are performed for at least two different configurations of at least one of the first set of sensing structures and the second set of sensing structures; and
   the evaluation result provided in step d) is based on the respective sensing signals provided for each sensing structure in the plurality of sensing structures for each of the at least two different configurations.

5. The method according to claim 1, wherein, in step a), the potential difference between each sensing structure in the first set of sensing structures and each sensing structure in the second set of sensing structures is changed by changing a potential of each sensing structure in the second set of sensing structures and keeping a potential of each sensing structure in the first set of sensing structures constant.

6. The method according to claim 1, wherein a number of sensing structures in the second set of sensing structures is greater than a number of sensing structures in the first set of sensing structures.

7. The method according to claim 1, wherein each sensing structure in the first set of sensing structures is separated from each sensing structure in the second set of sensing structures by at least one intermediate sensing structure.

8. The method according to claim 7, wherein a potential of the at least one intermediate sensing structure is controlled to prevent a change in potential difference between the at least one intermediate sensing structure and the sensing structure in the first set of sensing structures.

9. The method according to claim 1, wherein:
   the sensing structures are arranged in an array having rows and columns of sensing structures;
   the first set of sensing structures comprises at least one row or at least one column of sensing structures; and
   the second set of sensing structures comprises at least one row or at least one column of sensing structures.

10. The method according to claim 1, wherein, in step a), the sensing signal indicative of the strength of the capacitive coupling is based on a first sampling carried out before the potential difference has been changed and a second sampling carried out after the potential has been changed.

11. The method according to claim 1, further comprising the step of:
    e) modifying at least one fingerprint sensor property based on the evaluation result.

12. A fingerprint sensor evaluation system for evaluating a dielectric structure covering a plurality of sensing structures comprised in a fingerprint sensor and defining a finger receiving surface of the fingerprint sensor, the fingerprint sensor evaluation system comprising:
    a fingerprint sensor interface for communication with the fingerprint sensor; and
    processing circuitry coupled to the fingerprint sensor interface, wherein the processing circuitry is configured to:
    acquire an image from the fingerprint sensor while the finger receiving surface of the fingerprint sensor remains untouched by a physical object;
    evaluate the dielectric structure covering the plurality of sensing structures in the fingerprint sensor based on the acquired image; and
    provide a result of the evaluation.

13. The fingerprint sensor evaluation system according to claim 12, wherein:

the fingerprint sensor is controllable to an evaluation mode in which the image provided by the fingerprint sensor indicates, for each sensing structure in the plurality of sensing structures, a capacitive coupling between the sensing structure and at least one other sensing structure in the plurality of sensing structures; and the processing circuitry is further configured to control the fingerprint sensor to the evaluation mode before acquiring the image from the fingerprint sensor.

14. A fingerprint sensing system for determining a fingerprint representation of a finger, the fingerprint sensing system comprising:

a fingerprint sensor comprising a plurality of sensing structures covered by a dielectric structure, the fingerprint sensor being controllable between:

an evaluation mode in which an image provided by the fingerprint sensor indicates, for each sensing structure in the plurality of sensing structures, a capacitive coupling between the sensing structure and at least one other sensing structure in the plurality of sensing structures; and a fingerprint sensing mode in which an image provided by the fingerprint sensor indicates, for each sensing structure in the plurality of sensing structures, a capacitive coupling between the sensing structure and the finger; and the fingerprint evaluation system according to claim 12 connected to the fingerprint sensor, and configured to:

control the fingerprint sensor to the evaluation mode and acquire a first image;

control the fingerprint sensor to the fingerprint sensing mode and acquire a second image;

modify the second image based on the first image to form a modified second image; and determine the fingerprint representation based on the modified second image.

15. An electronic device comprising:

a fingerprint sensing system according to claim 14; and processing circuitry configured to:

acquire a fingerprint representation from the fingerprint sensing system;

authenticate a user based on the fingerprint representation; and perform at least one user-requested process only if the user is authenticated based on the representation.

\* \* \* \* \*